(12) United States Patent
Han et al.

(10) Patent No.: US 10,478,080 B2
(45) Date of Patent: Nov. 19, 2019

(54) ARRAY PHYSIOLOGICAL DETECTION SYSTEM AND OPERATING METHOD THEREOF

(71) Applicant: PIXART IMAGING INC., Hsin-Chu County (TW)

(72) Inventors: Wei-Ru Han, Hsin-Chu County (TW); Chih-Yuan Chuang, Hsin-Chu County (TW); Cheng-Nan Tsai, Hsin-Chu County (TW); Ren-Hau Gu, Hsin-Chu County (TW)

(73) Assignee: PIXART IMAGING INC., Hsin-Chu County (TW)

(*) Notice: Subject to any disclaimer, the term of this patent is extended or adjusted under 35 U.S.C. 154(b) by 879 days.

(21) Appl. No.: 14/955,463

(22) Filed: Dec. 1, 2015

(65) Prior Publication Data

US 2016/0220130 A1 Aug. 4, 2016

(30) Foreign Application Priority Data

Jan. 29, 2015 (TW) ............................ 104103138 A
May 25, 2015 (TW) ............................ 104116752 A (51) Int. Cl.
  *A61B 5/02* (2006.01)
  *A61B 5/026* (2006.01)
  *A61B 5/0295* (2006.01)
  *A61B 5/00* (2006.01)
  *A61B 5/024* (2006.01)

(52) U.S. Cl.
  CPC .......... *A61B 5/0261* (2013.01); *A61B 5/0295* (2013.01); *A61B 5/02416* (2013.01); *A61B 5/7278* (2013.01); *A61B 5/441* (2013.01); *A61B 5/7282* (2013.01); *A61B 2503/10* (2013.01)

(58) Field of Classification Search
  CPC . A61B 5/0261; A61B 5/02416; A61B 5/7278; A61B 5/0295; A61B 5/441; A61B 5/7282; A61B 2503/10
  See application file for complete search history.

(56) References Cited

U.S. PATENT DOCUMENTS

| 2003/0233048 A1* | 12/2003 | Silverman ............ A61B 5/0002 600/500 |
| 2009/0247885 A1* | 10/2009 | Suzuki ............... A61B 5/02416 600/500 |
| 2011/0137137 A1 | 6/2011 | Shin et al. |
| 2012/0045426 A1* | 2/2012 | St. Cyr ............... A61K 31/198 424/94.64 |
| 2014/0316286 A1 | 10/2014 | Addison et al. |
| 2015/0164347 A1* | 6/2015 | Pollonini ............. A61B 5/0261 600/323 |
| 2015/0269349 A1* | 9/2015 | Taylor ................. G06F 17/5009 703/11 |

FOREIGN PATENT DOCUMENTS

| CN | 1387824 A | 1/2003 |
| WO | 2011/026986 A1 | 3/2011 |
| WO | WO-2011026986 A1 * | 3/2011 ......... A61B 5/02416 |

* cited by examiner

*Primary Examiner* — Navin Natnithithadha
*Assistant Examiner* — Andrey Shostak
(74) *Attorney, Agent, or Firm* — Hauptman Ham, LLP (57) ABSTRACT

A physiological detection system including an array sensor and a processing unit is provided. The array sensor is configured to output array PPG signals. The processing unit is configured to construct a 3D energy distribution according to the array PPG signals to accordingly identify different microcirculation states.

15 Claims, 6 Drawing Sheets

FIG. 5

ARRAY PHYSIOLOGICAL DETECTION SYSTEM AND OPERATING METHOD THEREOF

RELATED APPLICATIONS

The present application is based on and claims priority to Taiwan Patent Application Serial Number 104103138, filed Jan. 29, 2015 and Taiwan Patent Application Serial Number 104116752, filed May 25, 2015, the disclosures of which are hereby incorporated by reference herein in their entirety.

BACKGROUND

1. Field of the Disclosure

The disclosure generally relates to a physiological detection system and, more particularly, to an array physiological detection system capable of detecting at least three dimensions of physiological characteristics and an operating method thereof.

2. Description of the Related Art

Nowadays, portable electronic devices and wearable electronic devices have become the daily necessities to many people. As the lifestyle changes, their functions have also been constantly developed and improved.

At the same time, health has become an important issue among people. Therefore, the portable electronic devices and the wearable electronic devices have also been gradually provided with physiological detection functions to meet the requirements of the users.

SUMMARY

In light of this, the present disclosure provides an array physiological detection system capable of detecting and recording at least three dimensions of physiological characteristics of the user, as well as an operating method thereof.

The present disclosure provides an array physiological detection system which generates a 3D distribution of the physiological characteristics via a plurality of sensing pixels respectively detecting the physiological characteristics of different tissue areas, as well as an operating method thereof.

The present disclosure further provides an array physiological detection system capable of generating a 3D distribution of the physiological characteristics of different detected tissue areas, recording the changes of the 3D distribution of the physiological characteristics over time, and accordingly identifying different microcirculation states, as well as an operating method thereof.

The present disclosure provides an array physiological detection system for detecting a change of skin microcirculation. The array physiological detection system includes a light source, a photosensitive array and a processing unit. The light source is configured to irradiate a light on a skin area, wherein the light penetrates a surface of the skin area and reaches a dermis of the skin area. The photosensitive array includes a plurality of photosensitive pixels. Each of the plurality of photosensitive pixels is configured to output a plurality of brightness signals as a photoplethysmography signal by continuously detecting an outgoing light that emits outwardly from the dermis of the skin area. The processing unit is configured to convert the photoplethysmography signals of the plurality of photosensitive pixels into a plurality of frequency domain data, calculate a variation value and an average value of the plurality of frequency domain data, and identify different microcirculation states according to a change of the variation value and a change of the average value.

The present disclosure further provides an operating method of an array physiological detection system configured to detect a change of skin microcirculation via a plurality of photosensitive pixels. The operating method includes the steps of: irradiating a light, by a light source, on a skin area such that the light penetrates a surface of the skin area and reaches a dermis of the skin area; continuously detecting an outgoing light that emits outwardly of the dermis of the skin area by each of the plurality of photosensitive pixels to output a brightness variation signal; converting the brightness variation signals of the plurality of photosensitive pixels into a plurality of frequency domain data; calculating a variation value of the plurality of frequency domain data; and identifying a microcirculation state according to a change of the variation value.

The present disclosure provides an array physiological detection system for detecting a change of skin microcirculation. The array physiological detection system includes a photosensitive array and a processing unit. The photosensitive array is configured to detect a microcirculatory data array of a dermis of a skin area. The processing unit is configured to detect different microcirculation states according to at least one change of the microcirculatory data array over time.

In the array physiological detection system and an operating method of said system, a 4D physiological detection system can be further generated by creating a 3D energy variation representative of a change of a 3D energy distribution of the physiological characteristics.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENTS

It should be noted that, wherever possible, the same reference numbers will be used throughout the drawings to refer to the same or like parts.

Figure 1:
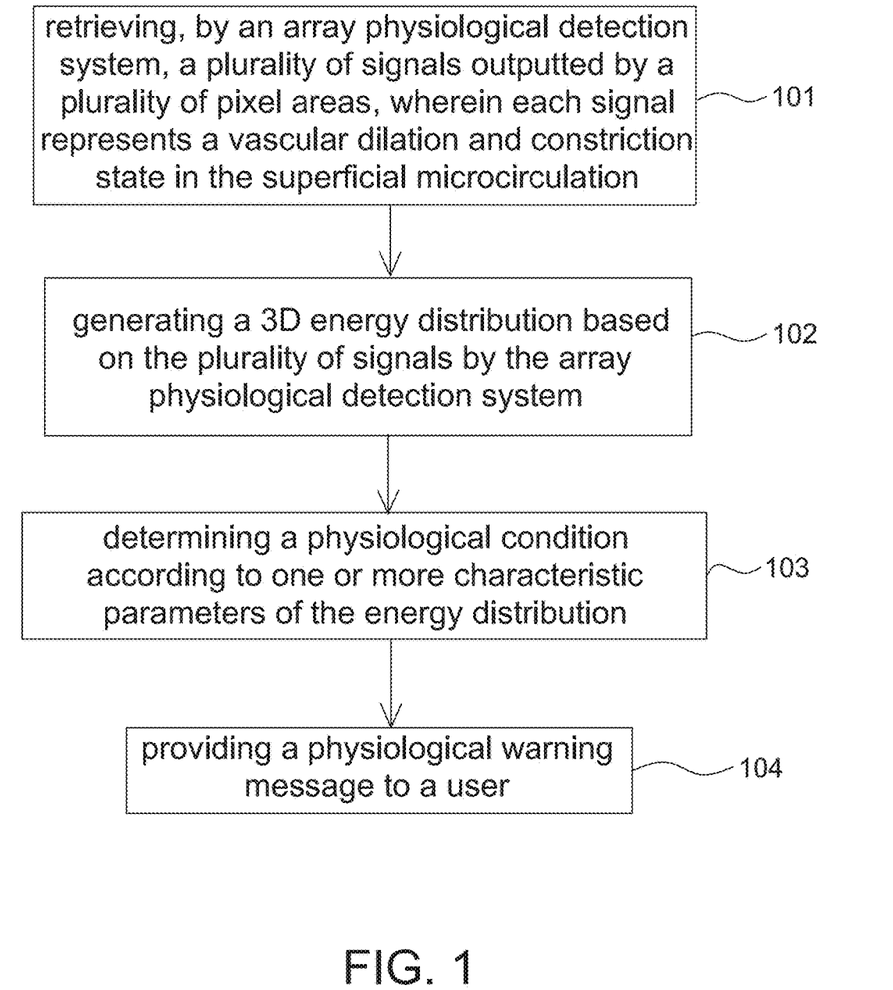
FIG. 1 is a flowchart for detecting a vascular dilation and constriction information in a superficial microcirculation, as performed by an array physiological detection system according to an embodiment of the present disclosure.

FIG. 1 shows a flowchart for detecting the dilation and constriction condition of the blood vessels in a superficial microcirculation, as performed by an array physiological detection system according to an embodiment of the present disclosure. The array physiological detection system detects a 3D energy distribution of a given skin area via the surface of the skin area of a user body part, so as to represent the vascular dilation and constriction condition in the superficial microcirculation. As such, the user will be able to monitor the health condition by himself/herself. In addition, the array physiological detection system according to the embodiment of the present disclosure may be arranged in a portable electronic device or a wearable electronic device to construct a portable physiological detection device. Therefore, a long-term self-supervision mechanism on the health condition is available and suitable for the user. For example, during a long period of time, the portable physiological detection device may monitor a 3D energy variation which is a change of the 3D energy distribution over time (i.e. the variation of the microcirculation information over time). Accordingly, the monitored results of the present array physiological detection system can be combined with the examination results of a short-term physical examination of a medical institution to provide highly reliable physiological information.

First, the array physiological detection system retrieves a plurality of signals outputted by a plurality of pixels. Each signal represents a vascular dilation and constriction state in the superficial microcirculation. The signals are photoplethysmography (PPG) signals as shown in the step 101. In order to obtain the plurality of signals indicative of the vascular dilation and constriction state in the superficial microcirculation, the array physiological detection system needs to obtain the vascular dilation and constriction information in the dermis and uses the information as a microcirculation data. This can be achieved via, for example, an optical detection mechanism where a proper wavelength of light is used such that the light is able to penetrate the epidermis but will not penetrate the dermis when the light is irradiated on the skin. Then, a photosensitive array is used to detect the plurality of signals indicative of the vascular dilation and constriction states in the microcirculation of the skin area. The photosensitive array includes a plurality of photosensitive pixels. Each photosensitive pixel is capable of generating a signal indicative of a vascular dilation and constriction state in the superficial microcirculation. Thus, various statistic values can be obtained for further application.

For instance, the light having a wavelength of 525 nm can be used and the skin penetration depth is smaller than 1 mm However, different wavelengths of lights can be used for different body parts when detecting the vascular changes in the superficial microcirculation of the dermis. Since the dermis has a depth of about 1 to 3 mm, the wavelength of the light should be properly selected such that the skin penetration depth is not larger than 3 mm, such as 300 to 900 nm.

Next, the array physiological detection system generates a 3D energy distribution based on the plurality of signals indicative of the vascular dilation and constriction state in the superficial microcirculation, as shown in the step 102. The 3D energy distribution refers to a spectral energy distribution. In the step, since the energies of the signals detected by the photosensitive pixels contain various frequencies, a certain frequency can be selected from the various frequencies for further analysis. In an embodiment, the current heartbeat frequency can be calculated from the plurality of signals indicative of the vascular dilation and constriction state in the superficial microcirculation. Then, for a magnitude signal detected by each of the plurality of photosensitive pixels, it can calculate a magnitude variation of the magnitude signal under the heartbeat frequency in order to represent the vascular dilation and constriction state in the superficial microcirculation.

The blood vessels in the superficial microcirculation dilate and constrict as the heart beats. Therefore, for a given photosensitive pixel having a signal, the magnitude of the signal varies more distinctly under the heartbeat frequency or a multiple of the heartbeat frequency than other frequencies other than the heartbeat frequency or the multiple of the heartbeat frequency.

Next, as shown in the step 103, the physiological condition can be determined according to one or more characteristic parameters of the energy distribution, such as the magnitude variation, an average value, the heartbeat frequency . . . etc. It will be described later in the specification on how the physiological characteristics are determined based on the characteristic parameters.

In the following, as shown in the step 104, a physiological warning message can be provided to the user. Accordingly, the user is able to adjust his/his daily schedule and activities.

Figure 2A:
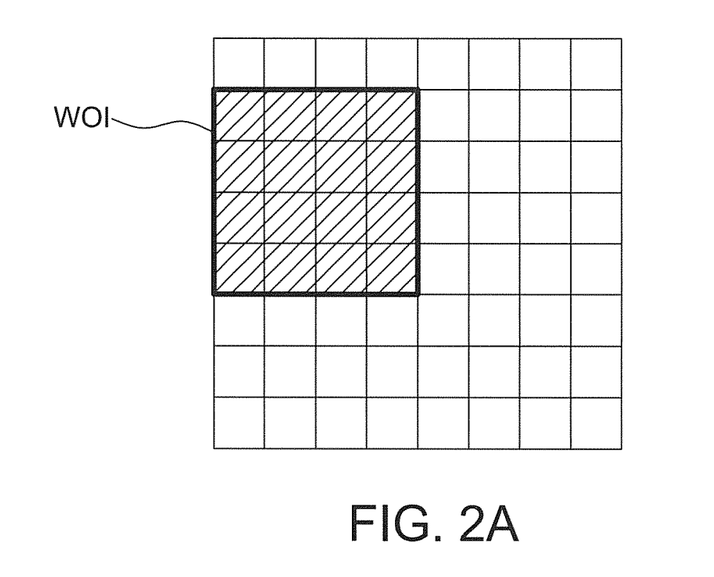
FIG. 2A shows an image frame and a window of interest (WOI) of the image frame as retrieved by the array physiological detection system of an embodiment of the present disclosure.
Figure 2B:
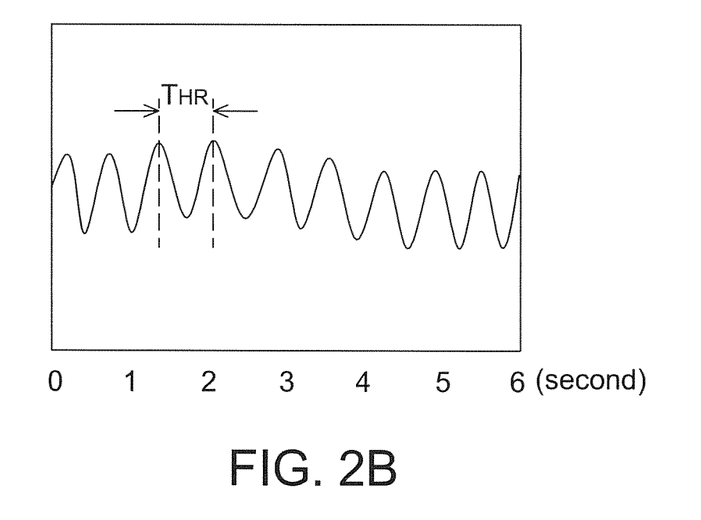
FIG. 2B shows a brightness variation of a plurality of image frames as retrieved by the array physiological detection system of an embodiment of the present disclosure.
Figure 2C:
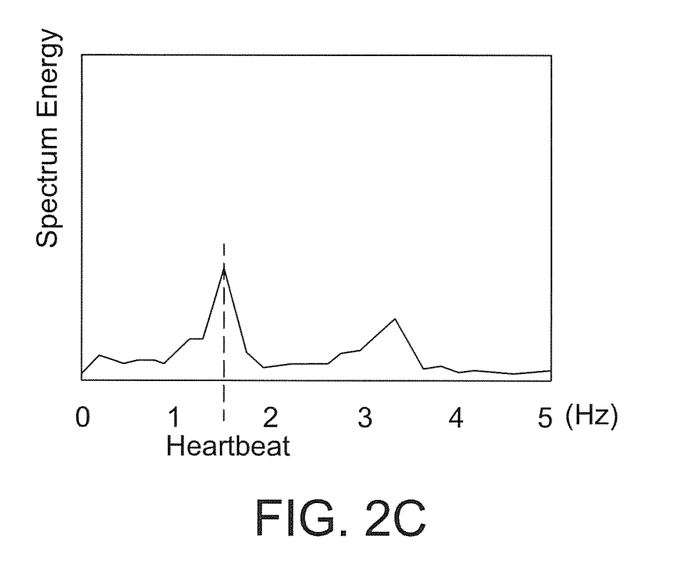
FIG. 2C is a spectrum of a plurality of signals indicative of the vascular dilation and constriction states in the superficial microcirculation, as detected by the array physiological detection system of an embodiment of the present disclosure.
Figure 2D:
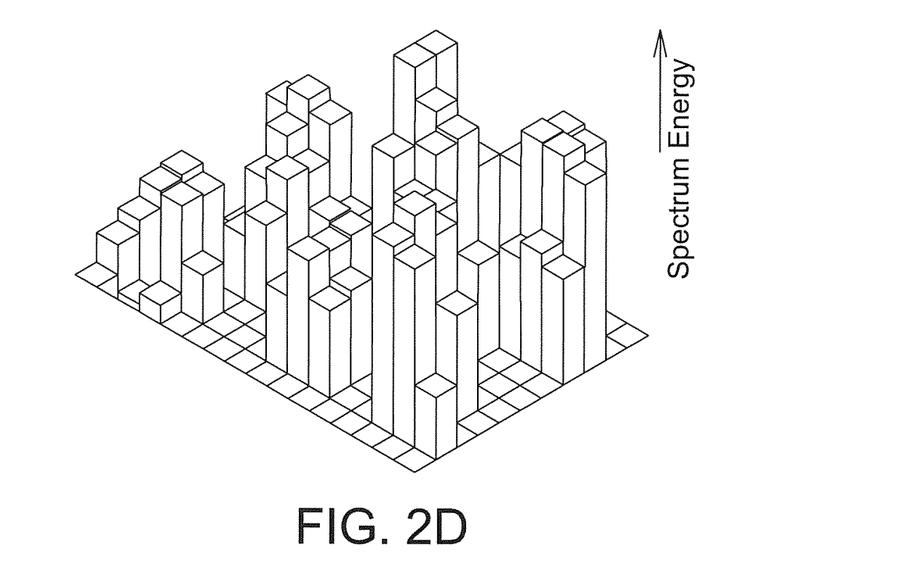
FIG. 2D is an energy distribution diagram of a plurality of pixel areas under a current heartbeat frequency, as detected by the array physiological detection system of an embodiment of the present disclosure.

FIGS. 2A to 2D show a process for detecting the vascular dilation and constriction states in the superficial microcirculation according to the array physiological detection system of the embodiment of the present disclosure. As an example of an optical physiological detection system, FIG. 2A shows a retrieved image frame and a retrieved window of interest (WOI) of the image frame. The size and location of the WOI are adjustable. FIG. 2B shows a brightness variation of a plurality of image frames or the WOIs of the image frames during a period of time, such as 6 seconds, for example. The brightness variation represents the vascular dilation and constriction state in the superficial microcirculation. FIG. 2C shows a spectrum of the plurality of signals indicative of the vascular dilation and constriction state in the superficial microcirculation. The spectrum is obtained by converting the brightness variation of FIG. 2B (namely, the plurality of signals indicative of the vascular dilation and constriction state in the superficial microcirculation) into the frequency domain. The spectrum also shows a current heartbeat frequency. FIG. 2D shows an energy distribution array consisting of a plurality of energy values of a plurality of pixel areas. Namely, the energy distribution array shows a magnitude distribution of the plurality of pixel areas. In FIG. 2D, the height of each bar represents an individual spectral energy under the current heartbeat frequency. It can be observed from FIG. 2D that the detected results (energy values) vary from pixel to pixel, which exhibits a change in the physiological characteristics (such as the distribution or functioning of the capillaries in the dermis), as described later.

The present disclosure can determine a state of motion according to different microcirculation states. For example, there are four microcirculation states, namely (I) pre-exercise state, (II) warm up completion state, (III) in-exercise state; and (IV) post-exercise cooling state.

Figure 3A:
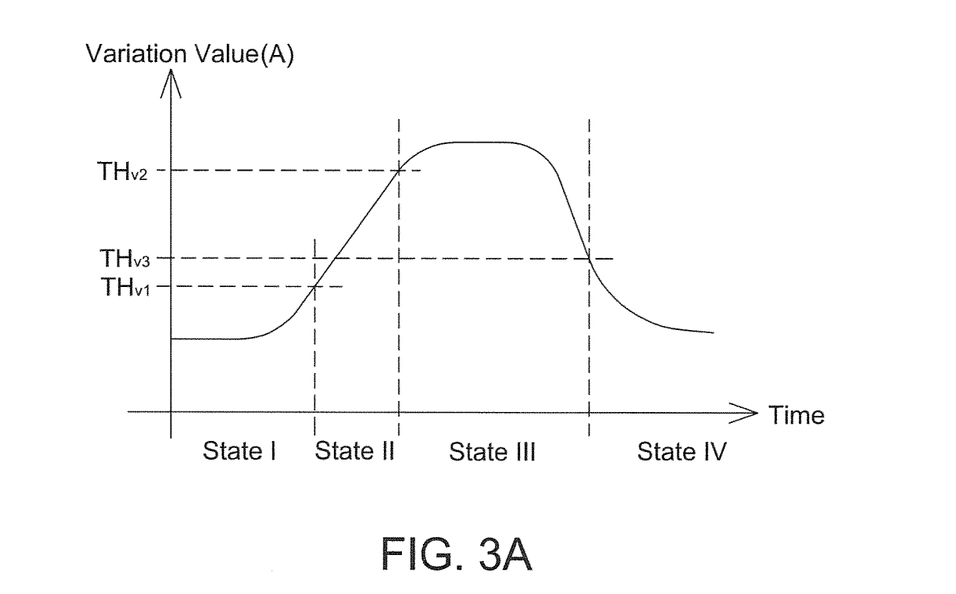
FIG. 3A is a change of a variation value detected by an array physiological detection system of an embodiment of the present disclosure.
Figure 3B:
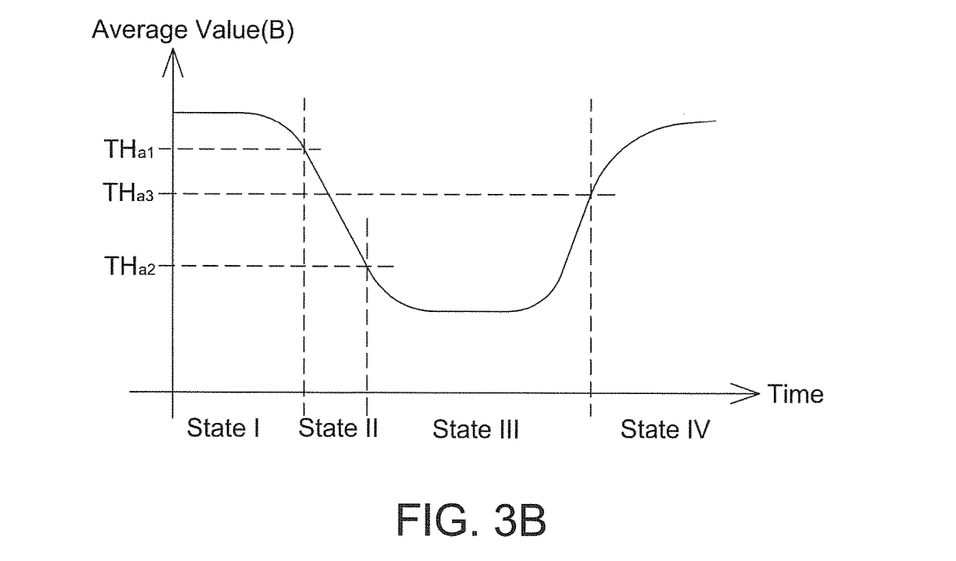
FIG. 3B is a change of an average value detected by an array physiological detection system of an embodiment of the present disclosure.

With reference made to FIGS. 3A and 3B. FIG. 3A is a change of the variation value detected by the array physiological detection system of the embodiment of the present disclosure. FIG. 3B is a change of the average value detected by the array physiological detection system of the embodiment of the present disclosure.

When the user is in the pre-exercise state (I), the magnitude variation (A) of the magnitude signal is not large, but the average value (B) of the magnitude signal is large.

When the user is in the warm up completion state (II), the magnitude variation (A) of the magnitude signal gradually increases, but the average value (B) starts to decrease. When the average value (B) of the magnitude signal is smaller than a warm up average threshold (such as THa1), it indicates that the warm up is completed. Alternatively, if the average value (B) of the magnitude signal is smaller than the warm up average threshold (such as THa1) and the magnitude variation (A) of the magnitude signal is larger than a warm up variation threshold (such as THv1), it indicates that the warm up is completed.

When the user is in the in-exercise state (III), the magnitude variation (A) of the magnitude signal is always large but the average value (B) of the magnitude signal is small. When the average value (B) of the magnitude signal is smaller than an in-exercise average threshold (such as THa2), it indicates that the user is doing the exercise. Alternatively, when the average value (B) of the magnitude signal is smaller than the in-exercise average threshold (such as THa2) and the magnitude variation (A) of the magnitude signal is larger than an in-exercise variation threshold (such as THv2), it indicates that the user is doing the exercise.

When the user is in the post-exercise cooling state (IV), the magnitude variation (A) of the magnitude signal gradually decreases, but the average value (B) of the magnitude signal starts to increase. When the average value (B) of the magnitude signal increases back to a value larger than a cooling average threshold (such as THa3), it indicates that the cooling process is completed. Alternatively, when the average value (B) of the magnitude signal increases back to a value larger than the cooling average threshold (such as THa3) and the magnitude variation (A) of the magnitude signal reduces back to a value smaller than a cooling variation threshold (such as THv3), it indicates that the cooling process is completed.

Although four microcirculation states, three variation thresholds and three average thresholds are shown in FIGS. 3A and 3B, it is noted that the numbers of the microcirculation states, the variation thresholds and the average thresholds are not limited and may be changed according to different applications. Thus, what is shown in FIGS. 3A and 3B is not used to limit the disclosure.

Figure 4:
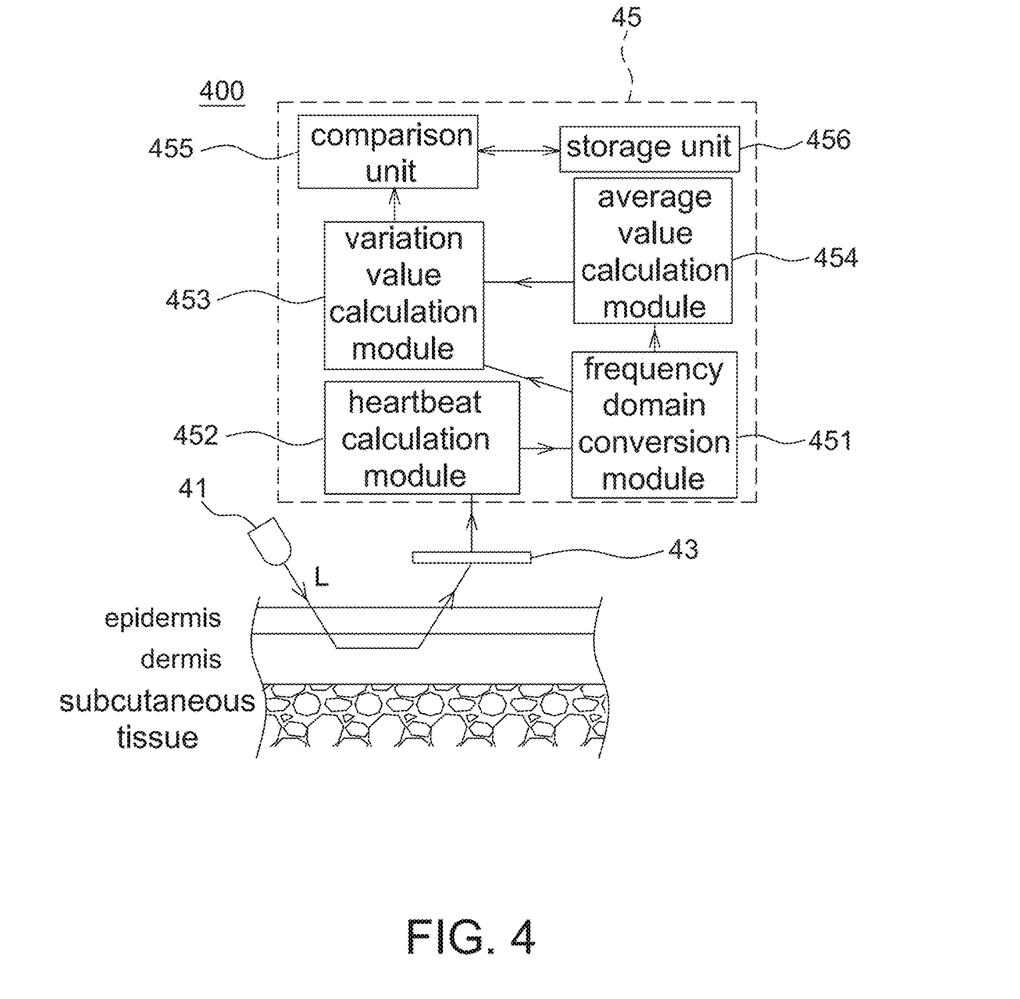
FIG. 4 is a systemic diagram of the array physiological detection system of an embodiment of the present disclosure.

FIG. 4 shows an array physiological detection system 400 according to an embodiment of the present disclosure. The array physiological detection system 400 is used to detect the vascular change in the microcirculation of the skin and includes a light source 41, a photosensitive array 43 and a processing unit 45.

The light source 41 can be a coherent light source, a non-coherent light source or a partial-coherent light source, such as a LED, a laser LED or the like. The light source 41 irradiates the light "L" on a skin area such that the light "L" penetrates the skin and reaches the dermis of the skin. Since the array physiological detection system 400 in the present disclosure simply detects the vascular change in the microcirculation of the dermis without detecting the physiological information of the subcutaneous tissue below the dermis, the light source 41 should have a proper wavelength where the light will not be able to reach the subcutaneous tissue below the dermis. The wavelength of the light source 41 is selected as 300 to 940 nm, for example.

The photosensitive array 43 is preferably an active image sensor array such as a CMOS image sensor. Thus, the size and location of the WOI (as shown in FIG. 2A) can be selected as desired according to the sampling result. For instance, the WOI can be determined based on the image quality and the brightness distribution. The photosensitive array 43 can not output the information detected by the pixels outside of the WOI. The photosensitive array 43 includes the plurality of photosensitive pixels. Each photosensitive pixel is used to continuously detect an outgoing light that emits outwardly from the dermis of the skin area, thereby outputting a plurality of brightness signals as a PPG signal (i.e. the vascular dilation and constriction indication signals in the superficial microcirculation), as shown in FIG. 2A. In some embodiments, the brightness signal is a digital signal, and the photosensitive array 43 can include an analogous-to-digital converter (ADC) for converting analogous signals into digital signals.

The processing unit 45 is configured to convert the brightness signals of the plurality of photosensitive pixels (such as the PPG signal) into a plurality of frequency domain data (as shown in FIG. 2C), thereby obtaining the 3D energy distribution indicative of the vascular dilation and constriction states in the superficial microcirculation (as shown in FIG. 2D). The processing unit 45 also calculates a variation value and an average value of the plurality of frequency domain data and identifies different microcirculation states according to the changes of the variation value and the average value (as shown in FIG. 3B). The processing unit 45 can be any device capable of calculating the data outputted by a sensor array, such as a digital signal processor (DSP), a central processor (CPU) or a microcontroller (MCU).

The processing unit 45 performs the above calculations via software, hardware, firmware or any combination thereof. For example, the processing unit 45 includes a frequency domain conversion module 451, a heartbeat calculation module 452, a variation value calculation module 453, an average value calculation module 454, a comparison unit 455 and a storage unit 456. It is understood that although the various elements in FIG. 4 are directed to different calculation functions, all of the calculation functions are performed by the processing unit 45 since all of the elements are arranged in the processing unit 45. Moreover, the processing unit 45 can also include other calculation functions such as data filtering and amplification.

Other insignificant functions of the processing unit 45 are omitted in the specification.

For example, each of the plurality of photosensitive pixels of the photosensitive array 43 outputs a plurality of brightness signals which varies over time and is used as a PPG signal (as shown in FIG. 2B). Thus, the processing unit 45 calculates a heartbeat frequency according to the PPG signals.

In one embodiment, the frequency domain conversion module 451 converts the PPG signal (as shown in FIG. 2B) of each of the plurality of photosensitive pixels into a frequency domain data (as shown in FIG. 2C). The heartbeat calculation module 452 calculates an estimated heartbeat frequency according to the frequency domain data of each of the plurality of photosensitive pixels. Among the estimated heartbeat frequencies of the plurality of photosensitive pixels, the one with the highest statistic will be used as the heartbeat frequency. Namely, an estimated heartbeat frequency can be calculated for each of the plurality of photosensitive pixels. Thus, a plurality of heartbeat frequencies will be calculated for all of the photosensitive pixels. Among the plurality of heartbeat frequencies, the one that corresponds to the largest number of the pixels will be used as the heartbeat frequency. In this manner, it is able to reduce the error resulting from the noise and to improve the calculation accuracy.

The plurality of photosensitive pixels in an image frame (or in the WOI of the image frame) has a plurality of brightness signals outputted by the photosensitive array 43. Thus, in another embodiment, the plurality of brightness signals in each image frame (or in the WOI of the image frame) may be added by the processing unit 45 to calculate a sum of brightness. As a result, the plurality of image frames will have a plurality of sums of brightness. The heartbeat frequency may be calculated based on the plurality of sums of brightness. Namely, in this embodiment, the processing unit 45 calculates a sum of brightness for each of the plurality of image frames. For the plurality of image frames, the processing unit 45 calculates a variation of the sum of brightness, which is used as a PPG signal as shown in FIG. 2B. In this embodiment, the heartbeat calculation module 452 can calculate the heartbeat frequency in the time domain. For example, as shown in FIG. 2B, the heartbeat calculation module 452 calculates a reciprocal of a time internal THR. Alternatively, the variation of the sum of brightness may be converted into the frequency domain by the heartbeat calculation module 452 first, so as to generate a frequency domain data as shown in FIG. 2C. Then, the heartbeat calculation module 452 calculates the heartbeat frequency based on the frequency domain data. The heartbeat frequency is the one with the largest spectral energy shown in FIG. 2C. In other words, in this embodiment, FIG. 2B represents the variation of brightness for a single photosensitive pixel. FIG. 2B also represents a variation of the sum of brightness for the plurality of image frames. For a single photosensitive pixel having a variation of brightness, FIG. 2C can represent a frequency domain data of the variation of brightness thereof. For the plurality of image frames having a variation of the sum of brightness, FIG. 2C can represent a frequency domain data of the variation of the sum of brightness thereof. This is dependent on the application. In the present disclosure, a proper algorithm such as fast Fourier transform (FFT) may be used to perform the time to frequency domain conversion. However, this is not used to limit the disclosure.

Upon the determination of the heartbeat frequency, for each of the plurality of photosensitive pixels, the variation value calculation module 453 may generate a spectral energy value under the heartbeat frequency. As such, the 3D energy distribution (or an energy set) can be formed, as shown in FIG. 2D. The variation value calculation module 453 calculates an energy variation of the 3D energy distribution (or the energy set) which represents a magnitude variation. For example, an energy difference between two adjacent photosensitive pixels may be calculated, and the energy differences of all of the photosensitive pixels may be added to generate a sum of energy difference. Alternatively, for each photosensitive pixel having a respective energy value, an energy difference between the respective energy value of the photosensitive pixel and an average energy may be calculated. Then, the energy differences (associated with the average energy) of all of the photosensitive pixels may be added to generate a sum of energy difference (associated with the average energy). Still alternatively, a variance of the energy set can be calculated. However, the calculations of the variation value calculation module 453 are not limited to the above as long as the calculation module 453 is able to obtain the variation of the 3D energy distribution (or the energy set). In this embodiment, the variation value of the 3D energy distribution is a variation of the spectral energy under the heartbeat frequency.

After the heartbeat frequency is determined, the average value calculation module 454 generates a spectral energy value under the heartbeat frequency for each of the plurality of photosensitive pixels. As such, the 3D energy distribution (or 3D energy set) can be formed, as shown in FIG. 2D. The average value calculation module 454 calculates an average value of the 3D energy distribution (or 3D energy set) which represents a magnitude average value. In the embodiment, the average value is an average value of the spectral energy under the heartbeat frequency.

It is noted that although the 3D energy distribution (or 3D energy set) are calculated by the variation value calculation module 453 and the average value calculation module 454 in the above embodiment, the 3D energy distribution (or 3D energy set) can also be calculated by other components in the processing unit 45 such as the frequency domain conversion module 451 or the heartbeat calculation module 452.

In some embodiments, the processing unit 45 can also identify different microcirculation states based on a heartbeat frequency in addition to the changes of the variation value and the average value. Namely, in the specification, the processing unit 45 can identify different microcirculation states (such as the pre-exercise state, the warm up completion state, the in-exercise state and the post-exercise cooling state) based on any combination between the change of the variation value, the change of the average value, and the change of the heartbeat frequency. However, the microcirculation states are not limited to the above.

The comparison unit 455 can identify different microcirculation states by comparing the variation value with at least one variation threshold (such as THv1 to THv3 in FIG. 3A). The comparison unit 455 can also identify different microcirculation states by comparing the average value with at least one average threshold (such as THa1 to THa3 in FIG. 3B). In addition, the comparison unit 455 can identify different microcirculation states by comparing the heartbeat frequency with at least one heartbeat threshold. All of the above thresholds can be stored in the storage unit 456, which can be a conventional memory (but is not limited thereto).

Figure 5:
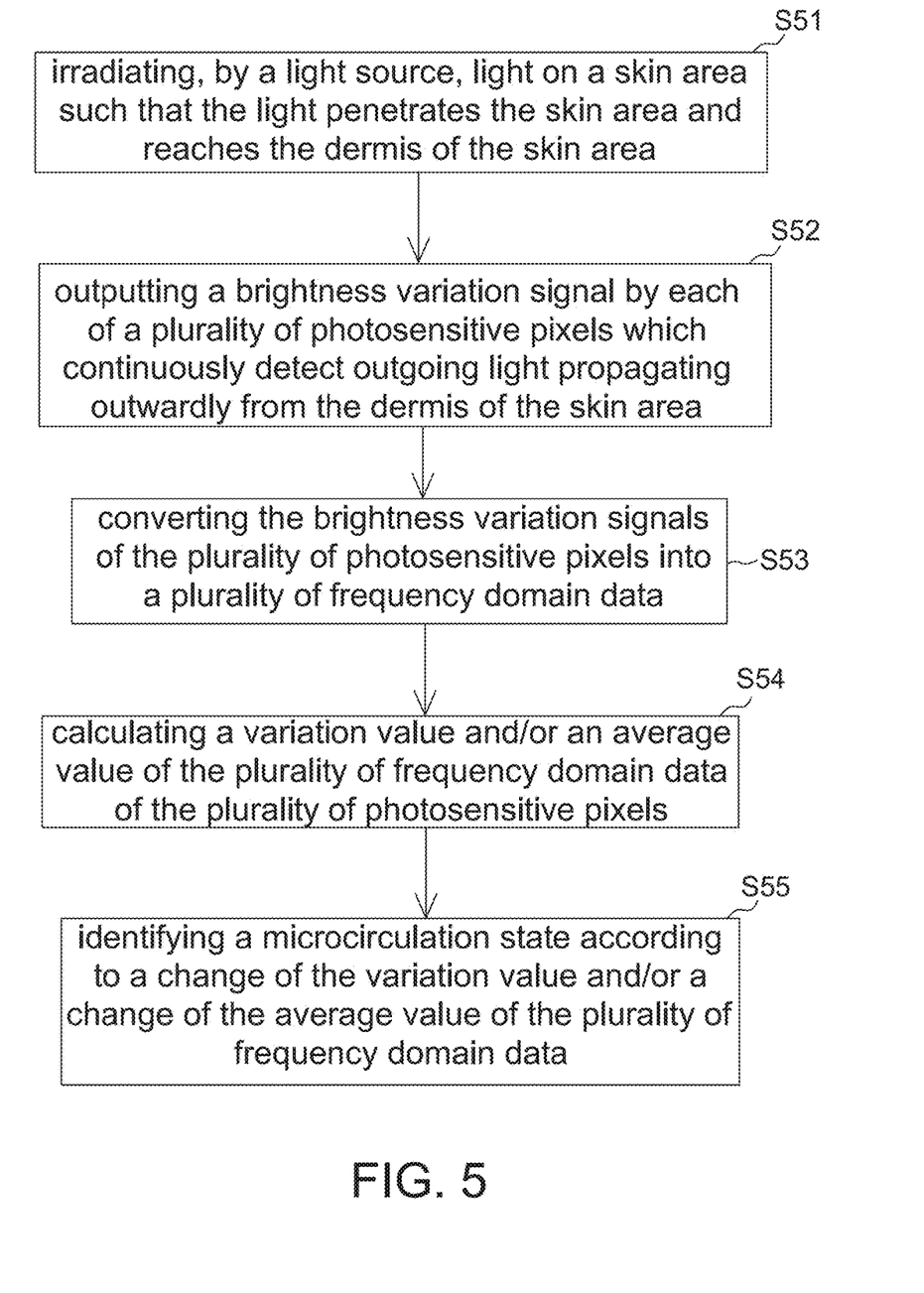
FIG. 5 is a flowchart of an operating method of the array physiological detection system of an embodiment of the present disclosure.

FIG. 5 shows a flowchart of an operating method of the array physiological detection system of the embodiment of the present disclosure, which is performed to detect the change of skin microcirculation via a plurality of photosensitive pixels. The operating method includes irradiating the light of a light source on a skin area such that the light of the light source penetrates the skin and reaches the dermis of the skin (S51), outputting a brightness variation signal by each of the plurality of photosensitive pixels continuously detecting the outgoing light that emits outwardly from the dermis of the skin area (S52), converting the brightness variation signals of the plurality of photosensitive pixels into a plurality of frequency domain data (S53), calculating a variation value and/or an average value of the plurality of frequency domain data of the plurality of photosensitive pixels (S54), and identifying a microcirculation state according to a change of the variation value and/or a change of the average value of the plurality of frequency domain data (S55).

The operating method of the embodiment of the present disclosure is described below with reference made to FIGS. 2A to 2D, 3A to 3B and 4-5.

In the step S51, the light source 41 irradiates the light "L" on the skin area so that the light "L" penetrates the surface of the skin area and reaches the dermis of the skin area. As stated above, the wavelength of the light "L" should be properly selected such that the light "L" does not penetrate the dermis of the skin. As such, the plurality of photosensitive pixels simply detects the vascular change in the superficial microcirculation without detecting the physiological information of the subcutaneous tissue below the dermis.

In the step S52, each of the plurality of photosensitive pixels of the photosensitive array 43 continuously detects the outgoing light that emits outwardly of the dermis of the skin area and respectively outputs a brightness variation signal, as the PPG signal in FIG. 2B. Therefore, the quantity of the PPG signals outputted by the photosensitive array 43 is the same as the quantity of the active pixels.

In the step S53, the processing unit 45 converts the brightness variation signals of the plurality of photosensitive pixels into a plurality of frequency domain data, as shown in FIG. 2C. Therefore, the quantity of the plurality of frequency domain data is also the same as the quantity of the active pixels.

In the step S54, the processing unit 45 calculates a variation value and/or an average value of the plurality of frequency domain data of the plurality of photosensitive pixels (S54). Since the characteristics of the plurality of frequency domain data are more noticeable under the heartbeat frequency or a multiple of the heartbeat frequency, the processing unit 45 calculates a heartbeat frequency according to the brightness variation signals of the plurality of photosensitive pixels prior to the calculations of the variation value and/or the average value. As stated above, the heartbeat frequency may be directly calculated in the time domain or may be calculated in a different manner in the frequency domain. Then, the 3D energy distribution (or the energy set) under the heartbeat frequency can be generated as shown in FIG. 2D. Next, based on the 3D energy distribution (or the energy set), the processing unit 45 can calculate an average value and/or a variation value of the spectral energy under the heartbeat frequency. The calculation of the variation value is not described herein as it has been discussed previously.

In the step S55, the processing unit 45 can identify a microcirculation state according to the change(s) of the variation value and/or the average value over time. The identification is carried out by comparing the variation value with at least one variation threshold and/or by comparing the average value with at least one average threshold (as shown in FIGS. 3A and 3B).

As stated above, in some embodiments, the processing unit 45 can also identify a microcirculation state based on the above factors along with the change of the heartbeat frequency over time.

Finally, the processing unit 45 notifies the user of the detected microcirculation state through images, sound or the like. However, this is not taken as a limited sense.

In summary, the present disclosure does not determine the state of motion via the percent of Maximal Heart Rate (MHR) or the user's own judgement. Instead, the state of motion is determined according to the vascular change in the superficial microcirculation associated with the blood circulation and distribution. In this mechanism, the vascular change in the superficial microcirculation of the skin can be represented by a plurality of brightness signals generated by the plurality of photosensitive pixels of the photosensitive array continuously detecting the outgoing lights that emit outwardly of the dermis. The plurality of brightness signals may form a PPG signal.

As stated above, the processing unit 45 can determine that the user is in the warm up completion state when the average value is smaller than a warm up average threshold (such as THa1) and/or when the magnitude variation (A) is larger than a warm up variation threshold (such as THv1). Furthermore, the processing unit 45 determines that the user is doing the exercise when the average value reduces back to a value smaller than an in-exercise average threshold (such as THa1) and/or when the magnitude variation (A) is larger than an in-exercise variation threshold (such as THv2). Moreover, the processing unit 45 determines that the user is in the post-exercise cooling state when the average value increases back to a value larger than a cooling average threshold (such as THa3) and/or when the magnitude variation (A) reduces back to a value smaller than a cooling variation threshold (such as THv3). The determination on the state of the motion in regard to the thresholds may vary according to the application.

In another embodiment, the vascular information in the superficial microcirculation of the skin can be detected in a non-optical manner (such as Doppler detection) as long as the required resolution is met. For example, the photosensitive pixel is preferably in a size from 5×5 μm to 10×10 μm, and the photosensitive array is preferably in a size from 240×240 μm to 480×480 μm. The detection is not limited to the optical detection. Namely, the physiological detection system always includes a sensor array and a processing unit irrespective of whether a light source is included. The sensor array is used to detect a microcirculatory data array in the dermis of the skin in order to reflect the states of different skin areas. The sensor array includes a plurality of pixel areas, which is in the form of a plurality of photosensitive pixels in an optical detection. In another detection mechanism, the plurality of pixel areas is in the form of a plurality of sensing pixels. In this regard, the processing unit determines different microcirculation states according to the changes of the microcirculatory data array over time. The changes of the microcirculatory data array include a change of the microcirculatory data array over time, as well as a change of the average value of the microcirculatory data array over time.

The present disclosure is suitable for use in a transdermal drug delivery system. The transdermal drug delivery system refers to a drug administration where, after a transdermal drug delivery is made, the drug takes effect when guided through the skin in a certain speed, absorbed by the blood vessels during the microcirculation, and finally circulated in the human body. As a result, the first pass effect of the liver can be avoided, and the deterioration on the effect of the drug caused by the gastrointestinal tract is also prevented. Advantageously, the number of times of drug delivery is reduced, the interval between the drug deliveries is prolonged, and the effective serum concentration is maintained.

The present disclosure can be used to monitor the absorption condition of the drug in the microcirculatory blood vessels. Specifically, when the magnitude variation of the microcirculatory data increases and the heartbeat frequency becomes larger, it can be determined that the transdermal drug delivery system is functioning. To the contrary, when all of the magnitude variation, the heartbeat frequency, and the average magnitude value of the microcirculatory data have been restored to the normal ranges as they were, it can be determined that the functioning of the transdermal drug delivery system is completed. Thus, further treatment can be carried out, such as the second run of drug delivery. In other words, the array physiological detection system of the embodiment of the present disclosure is able to reflect the condition of drug delivery via the 3D spectral energy, thereby obtaining the effectiveness of the drug delivery.

Diabetic patients tend to have diseases such as atherosclerosis of native arteries of the extremities and peripheral neuropathy. The atherosclerosis of native arteries will cause the ischemic necrosis of the tissues, and the peripheral neuropathy will cause motor weakness and astereognosis. Since the microcirculatory blood vessels are innervated by sympathetic nerves, it is able to provide an early warning mechanism indicating whether the diabetic patients have contracted the aforementioned diseases via the supervision of the vascular change The present disclosure is able to monitor the vascular change of the microcirculatory blood vessels. When the microcirculation date presents a magnitude variation and an average value that decrease over time, it can be known that the functioning of the blood vessels is retrograding. In other words, the array physiological detection system of the embodiment of the present disclosure is able to reflect the degree of retrogression of the microcirculation, thereby obtaining the severity of illness.

The present disclosure is able to detect the pathological change of the patient. Specifically, an external excitation may be applied to the patient, and the microcirculatory response of the patient can be observed. For example, when observing whether the patient has a peripheral neuropathy, a cool and warm excitation is applied to the patient. In this regard, if the microcirculation presents a reduced magnitude variation and the heartbeat frequency does not increase, it indicates that the activity of the peripheral nerve is not high. In this case, a pathological change may be resulted.

The burned patients tend to have low blood capacity shock as well as increased fragility and permeability of the microcirculatory blood vessels due to the lack of local skin protection. In this situation, since the condition of the patients becomes worse quickly, the patients may have multiple organ dysfunction syndrome if the patients are not rescued in time. In this regard, the array physiological detection system of the embodiment of the present disclosure is able to detect the circulations of the peripheral tissues of the patients, thus monitoring the conditions of the patients and preventing the patients from a worse condition. In other words, the array physiological detection system of the embodiment of the present disclosure is able to reflect the operational status of the microcirculation via the 3D energy spectrum, thereby reflecting the change on the conditions of the patients.

It has been proven that the hyperbaric oxygen therapy is clinically effective in improving the microcirculations of the tissues after radiotherapy. The hyperbaric oxygen therapy exhibits an outstanding curative effect in treatment of radiative osteonecrosis and soft tissue necrosis. When the patient is receiving the hyperbaric oxygen therapy, the curative effect may be observed via the array physiological detection system of the present disclosure. Specifically, when the magnitude variation of the microcirculatory data increases and the heartbeat frequency becomes larger, it indicates that the activity of the microcirculatory blood vessels has been gradually recovered. The therapy is effective. In other words, the array physiological detection system of the embodiment of the present disclosure is able to reflect the recovering process of the microcirculation via the 3D energy spectrum. Therefore, the curative effect can be observed.

Shock is an onging phenomenon. When the tissues or organs of the human body are not provided with a sufficient amount of blood due to the inability of the circulation system to provide a proper metabolism, the tissues or organs in the body will have insufficient oxygen. As a result, the cell metabolism will be abnormal, causing a damage to, or death of, the cells. When the patient has a shock, the microcirculatory blood vessels will start to dilate. In this case, the condition of the patient may become worse if the situation is not properly handled.

When an alleviation mechanism is made to the shock, it can be observed whether the alleviation has taken effect or not through the use of the array physiological detection system of the embodiment of the present disclosure. If the average value of the magnitude signal is very large, the magnitude variation of the magnitude signal is not large and the heartbeat frequency remains relatively large, it indicates that the alleviation has not taken effect yet, and vice versa. In other words, the array physiological detection system of the embodiment of the present disclosure is able to reflect the recovering process of the microcirculation via the 3D energy spectrum. Therefore, the alleviation effect can be observed.

Heat exhaustion and heatstroke are typically seen in a case of excessively intensive exercise. In this situation, the blood circulation of the skin will increase. As a result, the amount of the blood that is pumped out by the heart should be increased. When the amount of blood is insufficient, the blood in the body will be reallocated such that the internal organs will be allocated with a smaller amount of blood and the skin tissues will be allocated with a larger amount of blood to facilitate the sweating process. As such, the heat in the body can be smoothly expelled. When the array physiological detection system of the embodiment of the present disclosure is used during the exercise, if it is detected that the average value of the magnitude signal is very large, the magnitude variation of the magnitude signal is not large, and the heartbeat frequency remains relatively large, the user will be reminded that he/she might have been in an intensive exercise and should take a break. In other words, the array physiological detection system of the embodiment of the present disclosure is able to reflect the blood allocation condition of the microcirculation via the 3D energy spectrum. Therefore, the cooling effect can be observed.

Microcirculation has the functions such as regulating the amount of the blood of the tissues, providing the cells with the nutrition, discharging the metabolite . . . etc. Through the array physiological detection system of the embodiment of the present disclosure, the corresponding temperature change of the peripheral tissue in the microcirculation can be detected. Namely, for the microcirculatory blood vessels of a local tissue, when the average value of the magnitude signal thereof is large, it indicates the temperature is increased, and vice versa. In other words, the array physiological detection system of the embodiment of the present disclosure is able to reflect the temperature condition of the microcirculation via the 3D energy spectrum. Therefore, the amount of blood in a local tissue can be observed.

For detecting the sympathetic nerves of the peripheral tissues of autistic patients, infants and pets, there has not been any useful and portable device available for detecting the microcirculatory blood vessels in the peripheral tissues. The blood vessel walls of the artery and arteriole of the microcirculatory blood vessels are formed by the smooth muscle. The artery and arteriole of the microcirculatory blood vessels are innervated by sympathetic nerves to control the opening and closing of the microcirculatory blood vessels, thereby determining the amount of blood supply of the tissues. Through the use of the array physiological detection system of the embodiment of the present disclosure, the activity of the sympathetic nerves may be surmised in an indirect manner. When the activity of the sympathetic nerves is high, the change of the microcirculatory blood vessels is also more obvious, and vice versa. In other words, the array physiological detection system of the embodiment of the present disclosure is able to reflect the condition of blood supply via the 3D energy spectrum. Therefore, the activity of the sympathetic nerves can be observed.

The array physiological detection system of the embodiment of the present disclosure can also be used to determine the functioning of the heart as well as detecting the systemic vascular defect and sclerosis. After all of the vascular dilation and constriction indication signals in the superficial microcirculation are integrated as a signal result, the signal result will have different energies under different frequencies. In general, the signals indicative of the energy is supposed to appear at the heartbeat frequency or a multiple of the heartbeat frequency while the energies of the signals will remain in a normal range. The range can vary from person to person. However, for the same user, the range should not have a significant change as time goes on. Therefore, if the signals indicative of the energy is at a frequency which is not a multiple of the heartbeat frequency or if the energies of the signals go out of the normal range as time passes, it indicates that the functioning of the heart or blood vessels of the user is abnormal. Further examination is required.

For example, when the signals indicative of the energy appears at a frequency which is not a multiple of the heartbeat frequency, it can indicate that the user has a cardiac dysfunction such as valve defect. When the energies of the signals have gone way beyond the normal range, it can indicate that the user has a vascular sclerosis. As a result, the heart needs to increase its power in pumping the blood throughout the body. In other words, the array physiological detection system of the embodiment of the present disclosure is able to reflect the abnormality of the microcirculation via the 3D energy spectrum. Therefore, the functioning of the heart can be observed.

In the above description, the magnitude variation refers to an energy variation of the 3D spectral energy, and the average value of the magnitude refers to an average value of the 3D spectral energy. The distribution of the 3D spectral energy is similar to what is shown in FIG. 2D. In addition, the quantity of the active pixels as mentioned above refers to a quantity of the pixels in the WOI. All of the values discussed in the specification are merely for explanation of the present disclosure and should not be used to limit the disclosure.

Although the present disclosure has been described in detail with reference to its presently preferable embodiment, it will be understood by one of ordinary skill in the art that various modifications can be made without departing from the spirit and the scope of the present disclosure, as set forth in the appended claims.

What is claimed is:

1. An array physiological detection system, arranged in a wearable electronic device, and configured to detect a change of skin microcirculation, the array physiological detection system comprising:

a light source configured to be arranged facing a skin area of a user to irradiate a light on the skin area, wherein the light penetrates a surface of the skin area and reaches a dermis of the skin area;

a photosensitive array including a plurality of photosensitive pixels arranged in an array and configured to be arranged facing the skin area of the user, wherein each of the plurality of photosensitive pixels is configured to output a plurality of brightness signals as a photoplethysmography signal by continuously detecting an outgoing light that emits outwardly from the dermis of the skin area; and     a processing unit connecting to the photosensitive array to receive the photoplethysmography signals and configured to         convert the photoplethysmography signals of the plurality of photosensitive pixels respectively into a plurality of frequency domain data, each of the photosensitive pixels in the array having an energy value associated with a selected frequency of the corresponding frequency domain data,         calculate a variation value, which is a sum of energy differences between the energy of every photosensitive pixel in the array and the average value, and an average value of the energy values of the plurality of frequency domain data,         identify different microcirculation states according to a change of the variation value and a change of the average value, and         notify the user of the identified microcirculation states through the wearable electronic device using images or sound.

2. The array physiological detection system as claimed in claim 1, wherein the light of the light source has a wavelength from 300 nm to 940 nm.

3. The array physiological detection system as claimed in claim 1, wherein the processing unit is further configured to identify the different microcirculation states according to the heartbeat frequency.

4. The array physiological detection system as claimed in claim 1, wherein the processing unit is further configured to calculate the heartbeat frequency according to a plurality of sums of brightness of a plurality of image frames outputted by the photosensitive array, and each of the plurality of sums of brightness is calculated by adding the brightness signals of a respective one of the plurality of image frames outputted by the plurality of photosensitive pixels.

5. The array physiological detection system as claimed in claim 1, wherein the processing unit is further configured to calculate a plurality of estimated heartbeat frequencies according to the plurality of frequency domain data of the plurality of photosensitive pixels, and the heartbeat frequency is one of the plurality of estimated heartbeat frequencies that has the highest statistic.

6. The array physiological detection system as claimed in claim 1, wherein the processing unit is configured to determine that the microcirculation state is in the warm up completion state when the average value is smaller than a warm up average threshold.

7. The array physiological detection system as claimed in claim 6, wherein the processing unit is configured to determine that the microcirculation state is in the in-exercise state when the average value is smaller than an in-exercise average threshold.

8. The array physiological detection system as claimed in claim 1, wherein the processing unit is configured to determine that the microcirculation state is in the warm up completion state when the average value is smaller than a warm up average threshold and when the variation value is larger than a warm up variation threshold.

9. The array physiological detection system as claimed in claim 8, wherein the processing unit is configured to determine that the microcirculation state is in the in-exercise state when the average value is smaller than an in-exercise average threshold and the variation value is larger than an in-exercise variation threshold.

10. The array physiological detection system as claimed in claim 9, wherein the processing unit is configured to determine that the microcirculation state is in the post-exercise cooling state when the average value increases to exceed a cooling average threshold from below the in-exercise variation threshold.

11. An operating method of an array physiological detection system for detecting a change of skin microcirculation via a plurality of photosensitive pixels arranged in an array, the array physiological detection system being arranged in a wearable electronic device and comprising a light source, the light source and the array being arranged to face a skin area of a user, the operating method comprising:
    irradiating a light, by the light source, on the skin area such that the light penetrates a surface of the skin area and reaches a dermis of the skin area;
    continuously detecting an outgoing light that emits outwardly of the dermis of the skin area by each of the plurality of photosensitive pixels to output a brightness variation signal;
    converting the brightness variation signals of the plurality of photosensitive pixels respectively into a plurality of frequency domain data, wherein each of the photosensitive pixels in the array has an energy value associated with a selected frequency of the corresponding frequency domain data;
    calculating a variation value of the plurality of frequency domain data, wherein the variation value is a sum of energy differences between the energy value of every photosensitive pixel in the array and an average value of the energy values;
    identifying a microcirculation state according to a change of the variation value; and
    notifying the user of the identified microcirculation state through the wearable electronic device using images or sound.

12. The operating method as claimed in claim 11, further comprising:
    identifying the microcirculation state further according to a change of the average value.

13. The operating method as claimed in claim 12, further comprising:
    comparing the average value with at least one average threshold.

14. An array physiological detection system, arranged in a wearable electronic device, and configured to detect a change of skin microcirculation, the array physiological detection system comprising:
    a photosensitive array having a plurality of photosensitive pixels arranged in an array and configured to be arranged facing a skin area of a user, the photosensitive array configured to detect a microcirculatory data array of a dermis of the skin area; and
    a processing unit connecting to the photosensitive array to receive the microcirculatory data array, and configured to
        convert the microcirculatory data array respectively into a plurality of frequency domain data, each of the photosensitive pixels in the array having an energy value associated with a selected frequency of the corresponding frequency domain data,
        detect different microcirculation states according to a change of a variation value of the plurality of frequency domain data over time, wherein the variation value is a sum of energy differences between the energy value of every photosensitive pixel in the array and an average value of the energy values, and
        notify the user of the identified microcirculation states through the wearable electronic device using images or sound.

15. The array physiological detection system as claimed in claim 14, wherein the processing unit is further configured to detect the different microcirculation states according to a change of the average value.

* * * * *